United States Patent [19]

Satzinger et al.

[11] 4,087,544
[45] May 2, 1978

[54] TREATMENT OF CRANIAL DYSFUNCTIONS USING NOVEL CYCLIC AMINO ACIDS

[75] Inventors: Gerhard Satzinger, Denzlingen; Johannes Hartenstein, Wittental; Manfred Herrmann, St. Peter; Wolfgang Heldt, Wasser, all of Germany

[73] Assignee: Warner-Lambert Company, Morris Plains, N.J.

[21] Appl. No.: 791,677

[22] Filed: Apr. 28, 1977

Related U.S. Application Data

[62] Division of Ser. No. 645,724, Dec. 31, 1975, Pat. No. 4,024,175.

[30] Foreign Application Priority Data

Dec. 21, 1974 Germany ............... 2460891

[51] Int. Cl.$^2$ ............... A61K 31/215; A61K 31/195
[52] U.S. Cl. ............... 424/305; 424/319
[58] Field of Search ............... 424/305, 319

[56] References Cited

U.S. PATENT DOCUMENTS 4,035,507  7/1977  Bodor et al. ............... 424/319

Primary Examiner—Frederick E. Waddell
Attorney, Agent, or Firm—Albert H. Graddis; Frank S. Chow; George M. Yahwak

[57] ABSTRACT

The present invention is concerned with new cyclic amino acids and with the preparation thereof.

11 Claims, No Drawings

TREATMENT OF CRANIAL DYSFUNCTIONS USING NOVEL CYCLIC AMINO ACIDS

This is a division, of application Serial No. 645,724 filed Dec. 31, 1975 now U.S. Pat. No. 4,024,175 as of 17 May 1977.

Compounds of the general formula:

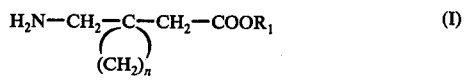

wherein $R_1$ is a hydrogen atom or a lower alkyl radical and $n$ is 4,5, or 6; and the pharmacologically compatible salts thereof, have been found to possess valuable pharmacodynamic properties.

Lower alkyl radicals according to the present invention are straight or branched chain alkyl radicals containing up to 8, and preferably up to 4 carbon atoms, especially methyl, ethyl, isopropyl and tert.-butyl radicals.

The compounds of general formula (I) show hypothermal and, in some cases, narcosis-potentiating or sedating properties. They are also characterized by an extremely low toxicity. In animal experiments, there was, surprisingly, also found a remarkable protective effect against cramp induced by thiosemicarbazide. Some of the compounds according to the present invention also possess a considerable protective action against cardiazole cramp. Thus these new compounds (I) can be used for the therapy of certain cerebral diseases, for example, they can be used for the treatment of certain forms of epilepsy, faintness attacks, hypokinesia and cranial traumas. They also bring about an improvement of the cerebral functions. Consequently, they are also especially useful for the treatment of geriatric patients.

The compounds of general formula (I) according to the present invention can be prepared, for example, by one of the following methods:

(a) converting a compound of the general formula:

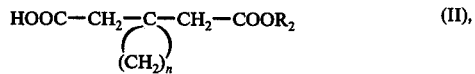

wherein $R_2$ is an alkyl radical containing up to 8 carbon atoms and $n$ has the same meaning as above, via a reactive acid derivative thereof, into an azide which is then subjected to the Curtius rearrangement; or (b) subjecting a compound of the general formula:

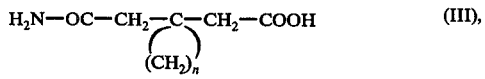

wherein $n$ has the same meaning as above, to the Hofmann rearrangement; or (c) subjecting a compound of the general formula:

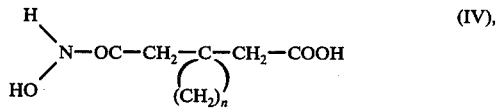

wherein $n$ has the same meanings as above, to the Lossen rearrangement.

When a free amino acid is obtained, it may be esterified to give a corresponding lower alky ester and/or the product obtained may be converted into a pharmacologically compatible salt by reaction with an acid or a base.

Since amino acids are amphoteric, pharmacologically compatible salts when $R_1$ is a hydrogen atom can be salts of appropriate inorganic and organic acids, for example, hydrochloric acid, sulphuric acid, phosphoric acid, acetic acid, oxalic acid, lactic acid, citric acid, malic acid, salicylic acid, malonic acid, maleic acid, succinic acid or ascorbic acid, but also, starting from the corresponding hydroxides or carbonates, salts with alkali metals or alkaline earth metals, for example, sodium, potassium, magnesium or calcium. Salts with quaternary ammonium ions can also be prepared with, for example, the tetramethyl-ammonium ion. Of course, when $R_1$ is a lower alkyl radical, it is only possible to form salts with acids.

The reaction of the compounds of general formula (II) takes place according to the well-known Curtius rearrangement. The free carboxyl group is first activated by conversion into a reactive derivative, for example an acid halide or a mixed anhydride, and subsequently reacted with an appropriate azide, for example, sodium azide. The acid azide thus obtained is then subjected to thermal decomposition in an organic solvent, for example, benzene, toluene or an alcohol, such as ethanol, during which nitrogen is split off and an intramolecular rearrangement to an isocyanate or, in the presence of an alcohol, to a urethane takes place. The isocyanates and the urethanes can easily be converted into the desired primary amines by basic or acid hydrolysis.

The well-known Hofmann rearrangement of compounds of general formula (III) also takes place via isocyanates. In this case, the acid amides are reacted with alkali metal hypohalites. Upon hydrolysis of the isocyanate formed by anionotropic rearrangement, the desired amine is formed, together with carbon dioxide.

The Lossen rearrangement of hydroxamic acids of general formula (IV) also takes a similar course. In this case, formally water is split off, the corresponding isocyanate first being formed, hydrolysis of which gives the desired amine. Usually the hydroxamic acids are reacted with bases via their O-acyl derivatives as, for example, the O-acetyl-, O-benzoyl- and preferably O-sulfonyl- derivatives.

If $R_1$ is to be a lower alkyl radical, the carboxyl group of the amino acids obtained is esterified under known protocols. Most simply, the reaction can be carried out by dissolving a free amino acid of general formula (I) or a salt thereof in an excess of the alcohol serving as the esterification component and the solution then saturated with hydrogen chloride. The corresponding amino acid ester hydrochloride is thus directly obtained. If it is desired to work without an excess of alcohol, then it is possible to employ the esterification methods known from amino acid chemistry, with masking of the amino group.

The compounds of general formula (II) used as starting materials can be prepared by reacting an acid anhydride of the general formula:

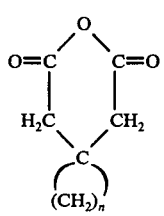

(V)

wherein n has the same meaning as above, with one mole of an alcohol of the general formula:

$$HO - R_2 \quad (VI),$$

wherein $R_2$ has the same meaning as above.

The compounds of general formula (V) are known (cf. J.C.S., 115, 686/1919; Soc., 99, 446; J.C.S., 117, 639/1920).

Some of the compounds of general formula (III), as well as processes for the preparation thereof, are known (cf. Austral. J.C., 13, 127/1960) and can, for example, also be prepared by reacting a compound of general formula (V) with ammonia. In this case, it is advantageous to work at the lowest possible temperature. However, it is also possible first, as described above, to prepare a hemi-ester, then to react the free carboxylic acid group with, for example, ethyl chloroformate and subsequently to carry out a reaction with ammonia.

The hydroxamic acids of general formula (IV) can be prepared analogously by reacting the anhydride of general formula (V) with hydroxylamine.

Because of their low toxicity, the compounds of general formula (I) according to the present invention can be administered enterally or parenterally within wide dosage ranges in liquid or solid form. As injection solution, water is preferably employed which contains the usual additives for injection solutions, such as stabilising agents, solubilising agents and/or buffers.

Additives of this kind include, for example, tartrate and citrate buffers, ethanol, complex-forming agents (such as ethylenediamine-tetraaacetic acid and the non-toxic salts thereof), as well as high molecular weight polymers (such as liquid polyethylene oxide) for viscosity regulation. Solid carrier materials include, for example, starch, lactose, mannitol, methyl cellulose, talc highly-dispersed silicic acids, high molecular weight fatty acids (such as stearic acid), gelatine, agar-agar, calcium phosphate, magnesium stearate, animal and vegetable fats and solid high molecular weight polymers (such as polyethylene glycol); compositions suitable for oral administration can, if desired, also contain flavouring and/or sweetening agents.

The individual dosage for the compounds according to the present invention can be 5 - 50 mg. parenterally and 20 - 200 mg. enterally.

Thus, the present invention also provides pharmaceutical compositions containing at least one compound of general formula (I) and/or at least one pharmacologically compatible salt thereof, in admixture with a solid or liquid pharmaceutical diluent or carrier.

The following Examples are given for the purpose of illustrating the present invention:

EXAMPLE 1

1-Aminomethyl-1-cyclohexane-acetic acid 5.6 ml. Triethylamine in 16 ml. anhydrous acetone are added dropwise, with stirring and cooling to 0° C., to a solution of 7.28 g. monomethyl 1,1-cyclohexanediacetate, whereafter a solution of 3.6 ml. ethyl chloroformate in 16 ml. anhydrous acetone is added thereto. The reaction mixture is further stirred for 30 minutes at 0° C. and then a solution of 3.4 g. sodium azide in 12 ml. water added dropwise thereto. The reaction mixture is stirred for 1 hour at 0° C., then poured into ice water and extracted three times with 50 ml. amounts of ice-cold toluene. The combined extracts are dried over anhydrous sodium sulphate at 0° C. and subsequently introduced dropwise into a flask pre-heated to 100° C. The mixture is then heated for a further hour under reflux and thereafter evaporated in a vacuum. The crude methyl 1-isocyanatomethyl-1-cyclohexane-acetate which remains behind is heated under reflux for 3 hours with 50 ml. 20% hydrochloric acid. After cooling the solution, it is extracted three times with 100 ml. amounts of chloroform to remove the 1-aminomethyl-1-cyclohexane-acetic acid lactam formed as a byproduct and the aqueous hydrochloric acid solution evaporated in a vacuum, whereby 1-aminomethyl-1-cyclohexaneacetic acid crystallises as the hydrochloride; m.p. 117°–118° C., after recrystallisation from acetone/methanol/ether. After recrystallization from methanol/ether the melting point of the product is 129°–133° C.

Analysis: $C_9H_{18}ClNO_2 \cdot 0.25 H_2O$: calc.: C 50.94%; H 8.79%; Cl 16.70%; N 6.60%; found: 51.03%; 8.56%; 16.34%; 6.84%.

By treatment with a basic ion exchanger and crystallisation from ethanol/ether, there is obtained pure 1-aminomethyl-1-cyclohexane-acetic acid; m.p. 162° – 166° C.

Analysis: $C_9H_{17}NO_2$: calc.: C 63.13%; H 10.01%; N 8.18%; O 18.69%; found: 63.20%; 9.61%; 7.95%; 19.02%.

The monomethyl 1,1-cyclohexane-diacetate used as starting material is prepared as follows:

32.8 g. 1,1-cyclohexane-diacetic anhydride are mixed with 7 g. anhydrous methanol and heated under reflux for 1 hour. After evaporation of the reaction mixture in a vacuum, 37.5 g. monomethyl 1,1-cyclohexane-diacetate remains behind in the form of a yellowish oil.

EXAMPLE 2

Ethyl 1-aminomethyl-1-cyclohexane-acetate 10 g. of the 1-aminomethyl-1-cyclohexane-acetic acid, prepared according to Example 1, are dissolved in 50 ml. anhydrous ethanol and saturated at 0° C. with gaseous hydrogen chloride. The reaction mixture is left to stand overnight at ambient temperature, then evaporated in a vacuum and the residue recrystallised from ethanol/ether. Ethyl 1-aminomethyl-1-cyclohexane-acetate is obtained in the form of its hydrochloride; m.p. 161° – 163° C.

Analysis: $C_{11}H_{22}ClNO_2$: calc.: C 56.04%; H 9.41%; N 5.94%; found: 55.93%; 9.28%; 5.94%.

EXAMPLE 3

1-Aminomethyl-1-cycloheptane-acetic acid 15.9 g. monomethyl 1,1-cycloheptane-diacetate are dissolved in 100 ml. anhydrous acetone and, in a manner analogous to that described in Example 1, first mixed with 8.1 g. triethylamine in 30 ml. acetone, thereafter with 9.8 g. ethyl chloroformate in 30 ml. anhydrous acetone and finally with 6.5 g. sodium azide in 20 ml. water. After the reaction has taken place, the reaction mixture is extracted as in Example 1 and the solution obtained of monomethyl 1,1-cycloheptane-diacetate azide is rearranged in toluene to the isocyanate. The methyl 1-isocyanatomethyl-1-cycloheptane-acetate obtained is boiled for 3 hours under reflux in 20% hydrochloric acid. Upon evaporation in a vacuum, 1-aminomethyl-1-cycloheptane-acetic acid separates out in the form of its hydrochloride, which is recrystallised from methanol/acetone/ethyl acetate; m.p. 69° – 72° C.

Analysis: $C_{10}H_{20}ClNO_2 \cdot 0.25\ H_2O$: calc.: C 53.12%; H 9.13%; Cl 15.68%; N 6.19%; O 15.88%; found: 53.29%; 9.03%; 15.73%; 6.16%; 15.77%.

The monomethyl 1,1-cycloheptane-diacetate used as starting material is prepared as follows:

13.7 g. 1,1-cycloheptane-diacetic anhydride are mixed with 2.36 g. anhydrous methanol in 10 ml. benzene and boiled under reflux for 2 hours. After evaporation, there are obtained 15.9 g. monomethyl 1,1-cycloheptane-diacetate, which is further worked up directly.

EXAMPLE 4

1-Aminomethyl-1-cyclopentane-acetic acid

Variant A:

17 g. 1,1-cyclopentane-diacetic acid monoamide are dissolved in 15 ml. water, together with 4 g. sodium hydroxide. The solution obtained is added dropwise at −10° C., while stirring, to a solution of sodium hypobromite, prepared by the dropwise addition of 19 g. bromine to a solution of 24 g. sodium hydroxide in 250 ml. water at −10° C. The reaction mixture is allowed to warm up to ambient temperature, while stirring, and thereafter heated to 60° C. for 2 hours.

After acidification with 12N hydrochloric acid, the reaction mixture is extracted three times with 150 ml. amounts of methylene chloride and the aqueous phase evaporated in a vacuum. The crude 1-aminomethyl-1-cyclopentane-acetic acid hydrochloride is obtained by digesting the residue with ethanol and evaporating the ethanolic solution. It is converted into the free amino acid by passing over an ion exchanger in the OH form. After stripping off the solvent and recrystallizing the residue from ethanol/ether, there is obtained pure 1-aminomethyl-1-cyclopentane-acetic; m.p. 171° – 172° C.

Analysis: $C_8H_{15}NO_2$: calc.: C 61.12%; H 9.62%; N 8.91%; O 20.25%; found: 60.78%; 9.37%; 8.93%; 19.96%.

The 1,1-cyclopentane-diacetic acid monoamide used as starting material is prepared as follows:

30 g. 1,1-cyclopentane-diacetic anhydride are mixed, while cooling, with 60 ml. of a 20% aqueous solution of ammonia. After the reaction has taken place, excess ammonia is removed in a vacuum and the solution is acidified with hydrochloric acid and then extracted with methylene chloride. Subsequently, the solvent is stripped off. The 1,1-cyclopentane-diacetate acid monoamide thus obtained can be further worked up directly.

Variant B:

5.88 g. 1,1-cyclopentane-diacetic anhydride are introduced, while cooling with ice water, into an ethanolic solution of hydroxylamine, prepared from 2.5 g. hydroxylamine crude benzene-sulfonate and the equivalent amount of sodium ethylate in 15 ml. anhydrous ethanol and subsequent filtration. The reaction mixture is further stirred for 1 hour at ambient temperature, the solution is evaporated in a vacuum and the curde hydroxamic acid taken up in 37 ml. 10% aqueous sodium carbonate solution. While cooling, 4.5 ml. benzene-sulphochloride is added thereto dropwise. The reaction mixture is further stirred for 1 hour at 25° C., mixed with 14 ml. of a 10% aqueous solution of sodium hydroxide and the reaction mixture then heated for 45 minutes to 100° C. After cooling, the solution is acidified with concentrated hydrochloric acid and then evaporated to dryness in a vacuum. The residue is treated with ethanol, filtered and the ethanolic solution concentrated somewhat. 1-Aminomethyl-1-cyclopentane-acetic acid thereby crystallises out as its benzene-sulfonate which, in the manner described in Variant A above, is converted into the free amino acid by means of an ion exchanger.

EXAMPLE 5

Sodium salt of 1-aminomethyl-1-cyclohexane-acetic acid

An aqueous solution of 1-aminomethyl-1-cyclohexane-acetic acid (Example 1) is mixed with an equimolar amount of a 1 n solution of sodium hydroxide. Thereafter the solution is evaporated in a vacuum until the beginning of crystallisation. After addition of isopropanol the precipitate obtained is filtered off and dried. The sodium salt of 1-amino-methyl-1-cyclohexane-acetic acid begins to sinter at about 150° C and has a melting point of 238° C.

Analysis: $C_8H_{16}NO_2Na \cdot \frac{1}{2}H_2O$: calc: C 53.46%, H 8.47%; found: 53.48%, 8.28%.

In the same manner, by reacting a molar aqueous solution of calcium hydroxide with a solution of 1-aminomethyl-1-cyclohexane-acetic acid, there is obtained the calcium salt.

The analogous ammonium salt is manufactured by reacting an ethanolic solution of 1-aminomethyl-1-cyclohexane-acetic acid with ammmonia. After evaporation in a vacuum the residue is crystallised from methanol/ether. The ammonium salt of 1-aminomethyl-1-cyclohexane-acetic acid thus obtained has a melting point of 145° – 150° C.

EXAMPLE 6

Methyl 1-aminomethyl-1-cyclohexane-acetate

In an analogous manner as described in Example 2, 1-aminomethyl-1-cyclohexane-acetic acid hydrochloride is reacted with methanol in the presence of hydrogen chloride. After evaporation in a vacuum the residue is recrystallised from methanol/ether to give pure methyl 1-aminomethyl-1-cyclohexane-acetate; m.p. 150° – 152° C. (hydrochloride)

Analysis: $C_{10}H_{20}ClNO_2 \cdot \frac{1}{4}H_2O$: calc.: C 53.15%; H 9.13%; Cl 15.69%; N 6.20%; found: 53.26%; 8.68%; 15.39%; 6.23%.

EXAMPLE 7 n-Butyl 1-aminomethyl-1-cyclohexane-acetate

A solution of 1-aminomethyl-1-cyclohexane-acetic acid hydrochloride in n-butanol is saturated with hydrogen chloride at 0° C. The reaction mixture is then heated to 110° C for two hours while hydrogen chloride is passed through. The solution thus obtained is then evaporated at 60° C and the residue stirred up with hexane is filtered and dried. n-Butyl 1-aminomethyl-1-cyclohexane acetate hydrochloride is obtained in form of a white powder having a melting point of 106° – 109° C.

Analysis: $C_{13}H_{26}ClNO_2 \cdot \frac{1}{4}H_2O$: calc.: C 58.20%; H 9.96%; Cl 13.21%; N 5.22%; found: 58.21%; 9.69%, 13.45%; 5.36%.

EXAMPLE 8

Sodium salt of 1-aminomethyl-1-cycloheptane-acetic acid

1-Aminomethyl-1-cycloheptane acetic acid is obtained from the hydrochloride of Example 3 by passing an aqueous solution through a basic ion exchange resin in the OH-form. The solution of the free amino acid is evaporated in a vacuum and the 1-aminomethyl-1-cycloheptane acetic acid obtained recrystallised from ethanol; m.p. 180° C.

Analysis: $C_{10}H_{19}NO_2$: calc.: C 64.83%; H 10.34%; N 7.56%; found: 64.55%; 10.32%; 7.35%.

According to Example 5 the free amino acid is reacted with a 1-molar aqueous solution of sodium hydroxide to give the sodium salt of 1-aminomethyl-1-cycloheptane-acetic acid, which after recrystallisation from methanol/isopropanol sinters above 140° C under slow decomposition.

The corresponding calcium salt is crystallising in the form of colourless platelets from water/acetone. The calcium salt of 1-aminomethyl-1-cycloheptane-acetic acid is sintering above 180° C without signs of melting.

EXAMPLE 9

Methyl 1-aminomethyl-1-cycloheptane-acetate

In an onologous manner as described in Example 2 1-aminomethyl-1-cycloheptane acetic acid hydrochloride is esterified with methanol in the presence of hydrogen chloride. After working up and crystallisation from isopropanol/ether/hexane, methyl 1-aminomethyl-1-cycloheptane-acetate is obtained as hydrochloride in the form of colourless crystals having a melting point of 115° - 116° C.

Analysis: $C_{11}H_{22}ClNO_2$: calc.: C 56.04%; H 9.41%; Cl 15.04%; N 5.94%; found: 55.70%; 9.24%; 14.94%; 6.05%.

EXAMPLE 10 n-Butyl 1-aminomethyl-1-cycloheptane-acetate . toluene sulfonate

In an analogous manner as described in Example 7, 1-aminomethyl-1-cycloheptane-acetic acid hydrochloride is esterified with n-butanol in the presence of hydrogen chloride to give n-butyl 1-aminomethyl-1-cycloheptane-acetate hydrochloride in the form of a syrup, which is mixed with benzene and an equivalent amount of p-toluene-sulfonic acid. The mixture is evaporated in a vacuum to dryness. After crystallisation from chloroform/ether/hexane n-butyl 1-aminomethyl-1-cycloheptane-acetate .p-toluene-sulfonate is obtained. m.p. 116° - 118° C.

Analysis: $C_{21}H_{35}NO_5S$: calc.: C 60.99%; H 8.53%; N 3.39%; found: 60.97%; 8.68%; 3.91%.

EXAMPLE 11

1-aminomethyl-1-cyclopentane-acetate . benzene-sulfonate

According to Example 1, monomethyl-1,1-cyclopentane-diacetate is subjected to the Curtius rearrangement via the azide form to give 1-aminomethyl-1-cyclopentane-acetic-acid hydrochloride having a melting point of 110° - 120° C after crystallisation from ethanol/ether.

Analysis: $C_8H_{16}ClNO_2$: calc.: C 49.61%; H 8.33%; N 7.23%; found: 49.93%; 8.12%; 7.23%.

The benzene-sulfonate of 1-aminomethyl-1-cyclopentane-acetic acid which is obtained by reaction of the free amino acid with benzene-sulfonic acid in ethanolic solution has a melting point of 171° - 173° C.

Analysis: $C_{14}H_{21}NO_5S$: calc.: C 53.31%; H 6.71%; N 4.44%; found: 53.44%; 6.77%; 4.58%.

EXAMPLE 12 n-Butyl 1-aminomethyl-1-cyclopentane-acetate

According to Example 7, 1-aminomethyl-1-cyclopentane-acetic acid hydrochloride is esterified with n-butanol to give n-butyl 1-aminomethyl-1-cyclopentane-acetate hydrochloride; m.p. 50° C.

The corresponding p-toluene sulfonate which is obtained after repeated evaporation of the benzene solution and by addition of an equimolar amount of p-toluene sulfonic acid and recrystallisation from chloroform/ether/hexane has a melting point of 86° - 87° C.

Analysis: $C_{19}H_{31}NO_5S$: calc.: C 59.19%; H 8.11%; N 3.63%; found: 59.35%; 7.99%; 3.88%.

We claim:

1. A method of treating certain forms of epilepsy, faintness attacks, hypokinesia and cranial traumas which comprises the enteral or parenteral administration to a mammal having such cranial dysfunction of an amount effective for such treatment of at least one compound or its pharmaceutically acceptable salt of the formula:

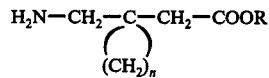

wherein R is hydrogen or a lower alkyl and n is 4, 5, or 6.

2. The method of claim 1 wherein the compound is 1-Aminomethyl-1-cyclohexane-acetic acid.

3. The method of claim 1 wherein the compound is Ethyl 1-aminomethyl-1-cyclohexane-acetate.

4. The method of claim 1 wherein the compound is 1-Aminomethyl-1-cycloheptane-acetic acid.

5. The method of claim 1 wherein the compound is 1-Aminomethyl-1-cyclopentane-acetic acid.

6. The method of claim 1 wherein the compound is Methyl 1-aminomethyl-1-cyclohexane-acetate.

7. The method of claim 1 wherein the compound is n-Butyl 1-aminomethyl-1-cyclohexane-acetate.

8. The method of claim 1 wherein the compound is Methyl 1-aminomethyl-1-cycloheptane-acetate.

9. The method of claim 1 wherein the compound is n-Butyl 1-aminomethyl-1-cycloheptane-acetate . toluene sulfonate.

10. The method of claim 1 wherein the compound is 1-Aminomethyl-1-cyclopentane-acetate . benzene-sulfonate.

11. The method of claim 1 wherein the compound is n-Butyl 1-aminomethyl-1-cyclopentane-acetate.

UNITED STATES PATENT AND TRADEMARK OFFICE

CERTIFICATE EXTENDING PATENT TERM
UNDER 35 U.S.C. § 156

PATENT NO.      :   4,087,544

DATED           :   May 2, 1978

INVENTOR(S)     :   Gerhard Satzinger et al.

PATENT OWNER    :   Warner-Lambert Company

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,720 DAYS from the date of expiration of the original patent term, May 2, 1995, with all rights pertaining thereto as provided by 35 U.S.C. § 156(b).

I have caused the seal of the Patent and Trademark Office to be affixed this 23rd day of April 1996.

Bruce A. Lehman
Assistant Secretary of Commerce and
    Commissioner of Patents and Trademarks